United States Patent [19]

Heier et al.

[11] 4,414,020
[45] Nov. 8, 1983

[54] COMPOSITION AND PROCESS FOR PROMOTING THE GROWTH OF CROP PLANTS

[75] Inventors: Karl H. Heier, Frankfurt am Main; Hans J. Nestler, Königstein; Hermann Bieringer, Eppstein; Klaus Bauer, Rodgau, all of Fed. Rep. of Germany

[73] Assignee: Hoechst AG, Frankfurt am Main, Fed. Rep. of Germany

[21] Appl. No.: 222,077

[22] Filed: Jan. 2, 1981

[30] Foreign Application Priority Data

Jan. 3, 1980 [DE] Fed. Rep. of Germany ....... 3000076

[51] Int. Cl.³ ...................... A01N 37/36; A01N 33/02
[52] U.S. Cl. .......................................... 71/108; 71/86; 71/87; 71/88; 71/92; 71/94; 71/95; 71/98; 71/100; 71/103; 71/105; 71/106; 71/111; 71/118; 71/121; 71/90
[58] Field of Search ..................... 71/108, 121, 88, 94, 71/90

[56] References Cited

U.S. PATENT DOCUMENTS

| | | | |
|---|---|---|---|
| 3,131,509 | 5/1964 | Hoffmann | 71/77 |
| 3,515,536 | 6/1970 | Hill et al. | 71/121 |
| 3,849,494 | 11/1974 | Middleton | 71/121 |
| 3,890,135 | 6/1975 | Middleton | 71/121 |
| 4,090,866 | 5/1978 | Simmons et al. | 71/108 |
| 4,152,137 | 5/1979 | Martin | 71/105 |
| 4,227,009 | 10/1980 | Koch et al. | 71/108 |
| 4,230,874 | 10/1980 | Pallos et al. | 71/77 |
| 4,294,772 | 10/1981 | Martin | 71/108 |

FOREIGN PATENT DOCUMENTS 47-37540 9/1972 Japan ..................................... 71/121

OTHER PUBLICATIONS

Campbell, "Phenoxyacetamidoximes", (1964), CA 61, pp. 8236–8237.

*Primary Examiner*—Glennon H. Hollrah
*Attorney, Agent, or Firm*—Curtis, Morris & Safford

[57] ABSTRACT

Compounds of the formula

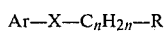

wherein Ar is (substituted) phenyl or naphthyl, X is oxygen, sulfur, SO or $SO_2$, n is 1–3 and R is CN or $C(NH_2)NOR_1$, (wherein $R_1$ is preferably hydrogen) are useful as safeners in crop protection.

8 Claims, No Drawings

COMPOSITION AND PROCESS FOR PROMOTING THE GROWTH OF CROP PLANTS

The present invention provides compositions having activity as safeners and containing a compound of the formula I $$Ar-X-C_nH_{2n}-R \qquad (I)$$

in which

Ar is phenyl optionally mono- or trisubstituted with chlorine or bromine, and/or monosubstituted with $CF_3$, $(C_1-C_4)$-alkyl, $(C_1-C_4)$-alkoxy, CN, $NO_2$, phenyl, benzyl or phenoxy in para-position; or is benzyl or phenoxy which in turn are optionally mono- or disubstituted in the phenyl nucleus with chlorine, bromine, CN, $NO_2$ or $CF_3$; or is naphthyl optionally mono- or disubstituted with chlorine, bromine, $(C_1-C_4)$-alkyl, CN, $NO_2$ or $CF_3$;

X is oxygen, sulfur, SO or $SO_2$;

n is 1, 2 or 3;

R is CN or $C(NH_2)NOR_1$;

$R_1$ is H, $(C_1-C_4)$-alkyl optionally substituted with chlorine, bromine,

CN, $NO_2$, $-COO(C_1-C_4)$-alkyl or $-CONR_2R_3$; $-COR_4$,

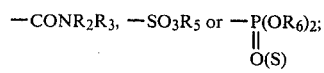

$R_2$ and $R_3$ each are H or $(C_1-C_{18})$-alkyl or, together with the nitrogen atom, form a piperidino, pyrrolidino or morpholino radical;

$R_4$ is $(C_1-C_3)$-alkyl, phenyl or benzyl; the latter two optionally being mono- or disubstituted in the phenyl nucleus with chlorine, bromine, CN, $NO_2$, $CF_3$ or $(C_1-C_3)$-alkyl;

$R_5$ is $(C_1-C_4)$-alkyl, phenyl or tolyl; and $R_6$ is $(C_1-C_4)$-alkyl.

The compounds of the formula I in which R is $C(NH_2)-NOH$ can be used alternatively in the form of their metal salts or acid addition products.

Preferred compositions are those which contain compounds of the formula I in which Ar is halophenyl, substituted phenoxyphenyl or naphthyl; X is oxygen; and

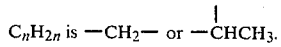

Examples of preferred individual compounds of the formula I are the following:

4-chlorophenoxyacetonitrile and -acetamidoxime,
α-(4-chlorophenoxy)propionitrile and -propionamidoxime,
2,4-dichlorophenoxyacetonitrile and -acetamidoxime,
3,4-dichlorophenoxyacetonitrile and -acetamidoxime,
4-bromo-2-chlorophenoxyacetonitrile and -acetamidoxime,
2,4,5-trichlorophenoxyacetamidoxime,
α-(4-bromo-2-chloro)phenoxypropionitrile and -propionamidoxime,
4-chloro-2-methylphenoxyacetonitrile and -acetamidoxime,
2-chloro-4-methylphenoxyacetonitrile and -acetamidoxime,
2,3-dichlorophenoxyacetonitrile and -acetamidoxime,
2-naphthyloxy-acetonitrile and -acetamidoxime,
α-(2,4-dichlorophenoxy)-propionitrile and -propionamidoxime,
4-chloro-phenylthioacetonitrile and -acetamidoxime,
3,4-dichlorophenylthio-acetonitrile and -acetamidoxime,
3,4-dichlorophenylsulfinyl-acetonitrile and -acetamidoxime,
3,4-dichlorophenylsulfonyl-acetonitrile and -acetamidoxime,
O-acetyl-4-chlorophenoxy-acetamidoxime,
O-(N-methyl-carbamoyl)-2,4-dichlorophenoxyacetamidoxime,
O-(N-octadecyl-carbamoyl)-2,4-dichlorophenoxyacetamidoxime,
O-(N,N-dimethyl-carbamoyl)-2,4-dichlorophenoxyacetamidoxime,
O-p-toluenesulfonyl-2,4-dichlorophenoxyacetamidoxime.

The compounds of the formula I as such are known and can be prepared according to methods known per se, or in an analogous manner; [J. Am. Chem. Soc. 69, 1690 (1947); Rocz. Chem. 45, 345 (1971); U.S. Pat. Nos. 3,139,455; 3,547,621 and 3,644,523; French Pat. No. 1,572,961; Japanese Pat. Nos. 42-9944 and 72,37,5407. Some of them have been proposed for herbicidal application.

Surprisingly, it has been observed that the compounds of the formula I, at low dosage, have growth-promoting and safening properties. Thus, they stimulate the growth of sprouting seeds and young plants, which becomes manifest by an enlarged root system, increased photosynthesis and faster development of the overground parts of the plants. Application of the compounds in a later stage of plant development results in increased fructification, earlier maturity and improved crop yield. Treatment of the seeds or seedlings with compounds of the formula I enables them to compete better with the non-stimulated weed flora. Furthermore, this treatment increases the chances of crop plants to grow under unfavorable conditions, for example on soils of low nutrient content.

A further important application field for the compounds of the formula I resides in their property of reducing or suppressing phytotoxic side effects of pesticides, especially herbicides, on selective use in crop plants, thus extending considerably the application scope of usual pesticides. Compounds having the property of protecting crop plants from phytotoxic damage by pesticides without adversely affecting their pesticidal action are called antidots or saferners.

Only a few example of herbicide antidots are hitherto known, e.g. N,N-diallyl-2,2-dichloroacetamide, [Can. J. Pl. Sci. 52, 707 (1972); German Pat. No. 2,218,097] or naphthalic anhydride [Weed. Sci. 19, 565 (1971); U.S. Pat. No. 3,131,509], and some oxime ethers and esters (German Offenlegungsschrift No. 2,808,317), especially in combination with thiocarbamate herbicides [see also F. M. Pallos and J. E. Cassida, "Chemistry and Action of Herbicide Antidots", Academic Press, New York/London, 1978].

Among the herbicides the phytotoxic side effects of which can be reduced by means of compounds of the formula I are phenyl ureas, triazines, carbamates, thiolcarbamates, halo-acetanilides, substituted phenoxy- and phenoxyphenoxy-carboxylic acid esters, pyridyloxy-, benzoxazyloxy- or benzothiazolyloxy-phenoxycarboxylic acid esters, furthermore benzoic acid derivatives, dimedonoxime derivatives and dinitro-aniline derivatives.

The following herbicides may be cited as examples:

(A) Herbicides of the phenoxycarboxylic ester type such as

α-[4-(2,4-dichlorophenoxy)-phenoxy]-propionic acid methyl ester,

α-[4-(4-bromo-2-chlorophenoxy)-phenoxy]-propionic acid methyl ester,

α-[4-(trifluoromethylphenoxy)-phenoxy]-propionic acid methyl ester.

α-[4-(2-chloro-4-trifluoromethylphenoxy)-phenoxy]-propionic acid methyl ester,

α-[4-(2,4-dichlorobenzyl)-phenoxy]-propionic acid methyl ester,

α-[4-(4-trifluoromethylphenoxy)-phenoxy]-2-pentene-1-carboxylic acid ethyl ester, α-[4-(3,5-dichloropyridyl-2-oxy)-phenoxy]-propionic acid ethyl ester, α-[4-(6-chlorobenzoxazol-2-yl-oxy)-phenoxy]-propionic acid ethyl ester or α-[4-(6-chlorobenzothiazol-2-yl-oxy)-phenoxy]-propionic acid methyl ester.

(B) Chloroacetanilide herbicides such as
N-Methoxymethyl-2,6-diethyl-chloroacetanilide,
N-[3'-methoxyprop-(2')-yl]-2-methyl-6-ethyl-chloroacetanilide,
N-(3-methyl-1,2,4-oxdiazol-5-ylmethyl)-chloroacetic acid-2,6-dimethylanilide.

(C) Thiocarbamates such as
S-ethyl-N,N-dipropylthiocarbamate or
S-ethyl-N,N-diisobutylthiocarbamate.

(D) Dimedon Derivatives such as
2-(N-ethoxybutyrimidoyl)-5-(2-ethylthiopropyl)-3-hydroxy-2-cyclohexene-1-one or
2-(1-allyloxyiminobutyl)-4-methoxycarbonyl-5,5-dimethyl-3-oxocyclohexenol.

(E) Herbicides of the dinitroaniline type such as N,N-di-n-propyl-2,6-dinitro-4-trifluoromethylaniline.

For application, the compounds of the formula I can be formulated with usual auxiliaries to give dusts, wettable powders, dispersions, emulsifiable concentrates etc., which contain from 2 to 80% of active substance, and which are used as such (dusting agents, pellets) or dissolved or dispersed before use in a solvent (water).

The quantitative ratio of antidot to herbicide may vary within wide limits of from 0.01 to 10 parts of antidots per part of herbicide. The optimum herbicide/antidot proportion depends on the particular type of herbicide and antidot and the kind of plant population to be treated, and can be determined according to the circumstances by corresponding tests.

Main application fields for the antidots of the invention are grain farming (wheat, rye, barley, oats, rice, corn, sorghum), furthermore crop farming of cotton, sugar beets, cane sugar, soybeans and the like.

Depending on their properties, the compounds of the invention can be used for pretreating (disinfecting) the seeds or cuttings of the crop plants, they may be applied to the furrows before sowing or pre- or post-emergent in the form of tank mixtures (the pre-emergence process including treatment of the area under cultivation before and after sowing). In principle, the antidot can be used before, after or simultaneous with the herbicide; preferred, however, is simultaneous application in the form of tank mixtures or ready-for-use formulations.

The following examples illustrate the invention.

EXAMPLE 1

Under open air conditions barley and wild oats were grown in pots up to the four-leaf stage and then treated with a test herbicide and an antidot of the invention. The substances were applied to the test plants alone or in combination in the form of aqueous emulsions or suspensions prepared from formulated emulsifiable concentrates or wetting powders. After treatment the plants were maintained at favorable growth conditions (18°–23° C., normal irrigation). After 3 weeks, the influence on the growth was evaluated by estimating the plant damage in percent. The results (see Table 1) prove that barley was protected by the antidot from damage by the herbicide without adversely affecting the efficiency of the herbicide against wild oats.

TABLE 1

| Effect of the compounds (damage in %) | | | |
|---|---|---|---|
| Compound | Dose kg AS/ha | barley | wild oat |
| $H_1$ | 1 | 0 | 93 |
|  | 2 | 12 | 100 |
|  | 4 | 28 | 100 |
| $A_1$ | 0.5 | 0 | 0 |
| $H_1 + A_1$ | 1 + 0.5 | 0 | 95 |
|  | 2 + 0.5 | 0 | 100 |
|  | 4 + 0.5 | 0 | 100 |
| $A_2$ | 0.5 | 0 | 0 |
| $H_1 + A_2$ | 1 + 0.5 | 0 | 93 |
|  | 2 + 0.5 | 0 | 100 |
|  | 4 + 0.5 | 0 | 100 |
| $A_3$ | 0.5 | 0 | 0 |
| $H_1 + A_3$ | 1 + 0.5 | 0 | 90 |
|  | 2 + 0.5 | 0 | 100 |
|  | 4 + 0.5 | 0 | 100 |
| $A_4$ | 0.5 | 0 | 0 |
| $H_1 + A_4$ | 1 + 0.5 | 0 | 93 |
|  | 2 + 0.5 | 0 | 100 |
|  | 4 + 0.5 | 2.0 | 100 |

AS = active substance
H = herbicide
A = antidote

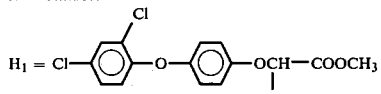

Diclofop-methyl (see German Offenlegungsschrift 2,223,894)

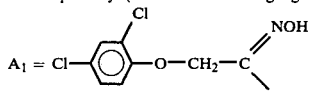

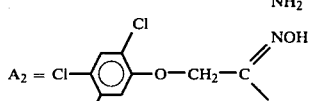

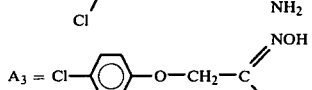

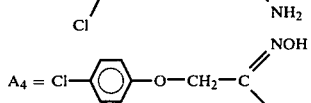

EXAMPLE 2

Crop and weed plants were grown in pots in a greenhouse up to the three-leaf stage. The herbicide antidot was applied to the green parts of the test plants in the form of aqueous suspensions at the doses as indicated. After drying of the spray liquor the test herbicide was applied by spraying. After 3 weeks in the greenhouse the damage of crop plants and weeds was evaluated optically in comparison with untreated controls. As results from Table 2, corn was efficiently protected by the antidot from damage by the herbicide.

TABLE 2

| Compound | Dose kg AS/ha | % damage Echinochloa Crus-galli | Zea mays |
|---|---|---|---|
| $H_2$ | 0.25 | 100 | 85 |
|  | 0.20 | 100 | 74 |
|  | 0.15 | 100 | 16 |
| $A_5$ | 1.0 | 30 | 0 |
| $H_2 + A_5$ | 0.25 + 1.0 | 100 | 28 |
|  | 0.20 + 1.0 | 100 | 24 |
|  | 0.15 + 1.0 | 100 | 8 |

H = herbicide
HS = active substance
A = antidote

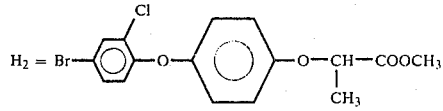

(see German Offenlegungsschrift 2,601,548)

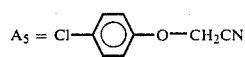

EXAMPLE 3

Seeds of barley (HD) and wild oats (AVF) were sown in pots on sandy loam, and grown under constant conditions in a greenhouse. In the three to four leaf stage the test plants were sprayed with diclofop-methyl ($H_1$), and the compounds of the invention alone and in combination (tankmix) at a constant ratio of 4:1 ($H_1$:A) but different application rates. After about 3 weeks, the damage caused by the herbicide to the crop plants and weeds was evaluated in comparison to untreated controls (indications in percent). The compositions of the invention had no herbicidal activity at all in barley and wild oats. When mixed with herbicides, however, the tolerability of the herbicides was considerably increased so that the crop plants remained undamaged, while the activity against wild oats was unchanged (see Table 3).

TABLE 3

| Compound | Dose kg AS/ha | % damage barley | wild oat |
|---|---|---|---|
| $H_1$ | 1.0 | 5 | 90 |
|  | 2.0 | 13 | 90 |
|  | 4.0 | 52 | 94 |
| $A_1$ | 2.0 | 0 | 0 |
|  | 4.0 | 0 | 0 |
| $A_4$ | 2.0 | 0 | 0 |
|  | 4.0 | 0 | 0 |
| $H_1 + A_1$ | 1.0 + 0.25 | 0 | 90 |
|  | 2.0 + 0.5 | 4 | 90 |
|  | 4.0 + 1.0 | 16 | 97 |
| $H_1 + A_4$ | 1.0 + 0.25 | 0 | 70 |
|  | 2.0 + 0.5 | 2 | 85 |
|  | 4.0 + 1.0 | 10 | 97 |

EXAMPLE 4

Seeds of sugar beets (BA), corn (ZM) and Echinochloa crus-galli (ECG) were placed in pots and covered with a thin layer of earth. The herbicidal compound N-(3-methyl-1,2,4-oxdiazol-5-yl-methyl)-chloroacetic acid-2,6-dimethylaniline ($H_3$; see German Offenlegungsschrift No. 2,842,284) and antidots of the invention were applied to the surface of the soil in the form of aqueous emulsions or suspensions prepared from formulated emulsifiable concentrates or wetting powders, separately as well as together and in different concentration or mixing ratios. After treatment the pots were placed in a greenhouse and left for 3 weeks under optimum growth conditions (18°–23° C., good irrigation). Subsequently, the influence of the substance on the growth of the crop plants and weeds was evaluated in percent. As results from Table 4, addition of the compositions of the invention considerably increased the tolerability of the herbicide against monocotyledonous as well as dicotyledonous crop plants without adversely affecting the action of the herbicide against weeds.

TABLE 4

| Compound | Dose kg AS/ha | % damage BA | ZM | ECG |
|---|---|---|---|---|
| $H_3$ | 2.50 | 50 | — | 100 |
|  | 1.25 | 25 | 74 | 100 |
|  | 0.60 | 0 | 76 | 100 |
|  | 0.30 | — | 45 | 100 |
| $A_1$ | 0.25 | 0 | — | 10 |
|  | 0.125 | 0 | — | 10 |
|  | 0.060 | 0 | — | 0 |
| $A_5$ | 2.50 | — | 17 | 78 |
|  | 1.25 | — | 5 | 73 |
|  | 0.60 | — | 0 | 58 |
| $H_3 + A_1$ | 2.50 + 0.06 | 15 | — | 100 |
|  | 1.25 + 0.06 | 0 | — | 100 |
|  | 0.60 + 0.06 | 0 | — | 100 |
|  | 1.25 + 0.25 | 15 | — | 100 |
|  | 1.25 + 0.125 | 8 | — | 100 |
| $H_3 + A_5$ | 1.25 + 0.6 | — | 7 | 100 |
|  | 0.6 + 0.6 | — | 5 | 100 |
|  | 0.3 + 0.6 | — | 0 | 100 |
|  | 1.25 + 1.25 | — | 10 | 100 |
|  | 0.6 + 1.25 | — | 10 | 100 |
|  | 0.3 + 1.25 | — | 7 | 98 |

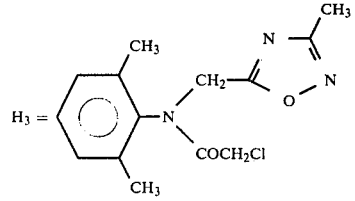

(see German Offenlegungsschrift 2,842,284)

EXAMPLE 5

Under greenhouse conditions, corn (ZM) and echinochloa (ECG) plants in the three-leaf stage were treated with aqueous emulsions or suspensions of diclofop-methyl ($H_1$) and the antidots of the invention, alone as well as in mixture with each other. About 3 weeks after treatment the damage of crop plants and weeds was evaluated in percent. As Table 5 clearly shows, the compounds of the invention practically reduce to zero the phytotoxicity of Illoxan ®, without decreasing the weed activity of the herbicide.

TABLE 5

| Compound | Dose kg AS/ha | % damage ZM | % damage ECG |
|---|---|---|---|
| H₁ | 0.6 | 63 | 100 |
|  | 0.3 | 50 | 100 |
|  | 0.15 | 9 | 99 |
| A₅ | 2.0 | 5 | 33 |
|  | 1.0 | 0 | 15 |
|  | 0.5 | 0 | 5 |
| H₁ + A₅ | 0.3 + 2.0 | 0 | 100 |
|  | 0.3 + 1.0 | 13 | 100 |
|  | 0.3 + 0.5 | 3 | 100 |
| H₁ + A₅ | 0.6 + 2.0 | 0 | 100 |
|  | 0.3 + 2.0 | 0 | 100 |
|  | 0.15 + 2.0 | 0 | 97 |

What is claimed is:

1. A herbicidal composition for promoting the safening of cereal crop plants comprising an effective amount of phenoxy alkanoic acid herbicide and an antidotally effective amount of an antidote of the formula $$Ar-O-C_nH_{2n}-R$$

or a metal salt or acid addition product thereof, in which Ar is phenyl mono-, di- or trisubstituted with chlorine or bromine; n is 1, 2 or 3 and R is $C(NH_2)NOH$ and wherein said herbicidal composition comprises from about 2 to about 80 percent by weight of antidote and herbicide, the ratio of antidote to herbicide being in the range of 0.125 to 7 parts antidote per part herbicide.

2. The composition defined in claim 1 wherein n is 1.

3. The composition defined in claim 1 wherein said herbicide is
α-[4-(2,4-dichlorophenoxy)-phenoxy]-propionic acid methyl ester,
α-[4-(4-bromo-2-chlorophenoxy)-phenoxy]-propionic acid methyl ester,
α-[4-(trifluoromethylphenoxy)-phenoxy]-propionic acid methyl ester,
α-[4-(2-chloro-4-trifluoromethylphenoxy)-phenoxy]-propionic acid methyl ester,
α-[4-(2,4-dichlorobenzyl)-phenoxy]-propionic acid methyl ester, and
α-[4-(4-trifluoromethylphenoxy)-phenoxy]-2-pentene-1-carboxylic acid ethyl ester.

4. The composition defined in claim 1 wherein said herbicide is α-[4-(2,4-dichlorophenoxy)-phenoxy]-propionic acid methyl ester.

5. The composition defined in claim 1 wherein said herbicide is α-[4-(4-bromo-2-chlorophenoxy)-phenoxy]-propionic acid methyl ester.

6. The composition defined in claim 1 wherein said antidote is 2,4-dichlorophenoxy acetamidoxime.

7. A method for protecting cereal crop plants against phytotoxic side effects of phenoxy alkanoic acid herbicides which comprises treating said plants, plant parts or the soils in which they grow with an effective amount of a composition as defined in claim 1, said antidote being applied to said plant before, after or simultaneously with said phenoxy alkanoic acid herbicide.

8. The method of claim 7 wherein said herbicide is as defined in claim 3.

* * * * *